(12) United States Patent
Marston

(10) Patent No.: US 8,356,993 B1
(45) Date of Patent: Jan. 22, 2013

(54) ORTHODONTIC APPLIANCE SYSTEM

(76) Inventor: Blake E. Marston, Brooklyn, NY (US)

( * ) Notice: Subject to any disclaimer, the term of this patent is extended or adjusted under 35 U.S.C. 154(b) by 32 days.

(21) Appl. No.: 12/778,522

(22) Filed: May 12, 2010

Related U.S. Application Data

(60) Provisional application No. 61/270,247, filed on Jul. 6, 2009.

(51) Int. Cl.
*A61C 7/00* (2006.01)

(52) U.S. Cl. .............................. 433/24; 433/6

(58) Field of Classification Search ................ 433/6, 8, 433/20, 16, 17, 22, 24, 9, 10–15, 7
See application file for complete search history.

(56) References Cited

U.S. PATENT DOCUMENTS

| | | | |
|---|---|---|---|
| 2,262,108 | A | 11/1941 | Linde |
| 4,880,380 | A * | 11/1989 | Martz ............................ 433/11 |
| 5,017,133 | A | 5/1991 | Miura |
| 5,055,039 | A * | 10/1991 | Abbatte et al. ................. 433/24 |
| 5,607,300 | A | 3/1997 | Tepper |
| 5,975,893 | A | 11/1999 | Chishti et al. |
| 6,607,382 | B1 | 8/2003 | Kuo et al. |
| 7,059,850 | B1 * | 6/2006 | Phan et al. ...................... 433/24 |
| 7,188,421 | B2 * | 3/2007 | Cleary et al. .............. 29/896.11 |
| 7,234,936 | B2 | 6/2007 | Lai et al. |
| 2004/0067463 | A1 | 4/2004 | Rosenberg |
| 2005/0191592 | A1 | 9/2005 | Farzin-Nia et al. |
| 2006/0234179 | A1 * | 10/2006 | Wen et al. .......................... 433/6 |
| 2007/0087301 | A1 | 4/2007 | Farzin-Nia et al. |
| 2007/0172788 | A1 * | 7/2007 | Hill, II et al. ................... 433/20 |
| 2007/0184398 | A1 * | 8/2007 | Cronauer .......................... 433/6 |
| 2008/0020337 | A1 * | 1/2008 | Phan et al. ........................ 433/6 |
| 2008/0063995 | A1 | 3/2008 | Farzin-Nia et al. |
| 2009/0035714 | A1 | 2/2009 | Kuo et al. |

OTHER PUBLICATIONS

Invisalign "Straighter Teeth Healthier Gums Beautiful Smiles", Align Technology, Inc., 2009 Brochure, 2 pages.
ESSIX Trademark of Raintree Essix, Inc., "Types of Tooth Movement Attainable With an Essix Appliance", pp. 61-63; "Force-Amplified Retention to Hold an Anterior Open Bite Closed", pp. 96-97; and "Other Applications of Essix Technology" pp. 109-111; total 9 pages. At least as early as Jul. 5, 2009.

\* cited by examiner

*Primary Examiner* — Cris L Rodriguez
*Assistant Examiner* — Matthew Seward
(74) *Attorney, Agent, or Firm* — McKee, Voorhees & Sease, P.L.C.

(57) ABSTRACT

A removable orthodontic appliance of discrete plastic sleeves, each being receivable over a corresponding tooth of a patient. Lingual clips are fastened to the corresponding tooth and which are engageable with corresponding structure of the sleeves for removably retaining each of said plastic sleeves to the corresponding tooth of the patient. Buccal brackets are fixably carried on a side of each of the sleeves positionally corresponding to a buccal surface of the corresponding tooth to which each of the sleeves is receivable. An arch wire is ligated to each of the buccal brackets to extend therebetween. The system can be conveniently removed for cleaning and adjustment.

1 Claim, 5 Drawing Sheets

ORTHODONTIC APPLIANCE SYSTEM

CROSS-REFERENCE TO RELATED APPLICATIONS

This application claims priority under 35 U.S.C. §119 of a provisional application Ser. No. 61/270,247 filed Jul. 6, 2009, and which application is hereby incorporated by reference in its entirety.

BACKGROUND OF THE INVENTION

The invention relates to an orthodontic appliance system, and more particularly, to an orthodontic appliance system which allows temporary removal of the active orthodontic components from the teeth of a patient undergoing orthodontic realignment, for teeth brushing, eating, etc., and facilitated reinstallation by the patient without the aid of a dentist.

For well over a century, orthodontists have been engaged in the process of repositioning teeth from a bad relationship, or "malocclusion," into a healthier and more esthetic arrangement. In order to move teeth, three elements are generally required: 1) force, 2) time and 3) space. The mouth responds to a sustained force placed on a tooth by rearranging, or "remodeling," the jawbone around the tooth. This remodeling creates space around the tooth allowing the tooth to move in the direction of the force. Not only does the tooth need space within the jawbone, but it is also imperative to have or create spacing between the teeth in order for movement to occur.

Over the years, orthodontists have invented devices, generally referred to as an "appliance," that permit clinicians to deliver sustained forces to the teeth. Braces, or "orthodontic brackets," are the classic appliances that most, if not all, orthodontists use. Braces consist of small brackets that are glued, or "bonded," to the teeth, and a wire is then inserted into the brackets and held into place with a ligature or clip. The brackets themselves do not deliver forces to the teeth. The force is applied when the wire is deflected and inserted into the slot on the bracket and held in by the ligature. The wire has a "memory," i.e., a characteristic by which the wire tends to return to its original shape, and in doing so, exerts a force on the bracket that is in turn transmitted to the tooth. Through the application of various types, shapes and sizes of wires, the teeth eventually align themselves into a more ideal occlusion. The technical term used among orthodontists to describe braces is "comprehensive fixed appliance."

Because of the obvious drawbacks of having foreign objects glued to a patient's teeth, appliances have been heretofore suggested that can be inserted and removed by the patient. A myriad of removable appliances have been developed over the years, but the vast majority of them are not "comprehensive" in nature. In other words, the removable appliances address specific movements or malocclusions, and are only used for a certain limited period of time. Treatment with removable appliances is often used in conjunction with braces or other appliances.

However, some companies offer clear aligners. Two notably are the ESSIX and INVISALIGN systems, and are presently being used comprehensively as an alternative to braces. Both the ESSIX and INVISALIGN appliances utilize clear plastic "aligners," or sheets of plastic, custom molded to an individual's teeth, to induce orthodontic movement.

INVISALIGN uses a technology called stereolithography (computer aided 3D prototyping) to fabricate a series of aligners from a digitized representation of the patient's mouth that has been scanned from a dental impression. Each aligner creates small, incremental movements, by placing pressure on the teeth in specific locations as determined by computer-generated models. As the series of aligners are worn, gradually the teeth are forced into a more desirable position.

The ESSIX appliance on the other hand, uses only one clear aligner that is manipulated by the clinician to apply specific forces to the teeth. To apply force with the ESSIX system, the orthodontist can either manipulate the plastic or add volume to the teeth.

All of the previously mentioned orthodontic appliances have both positive and negative attributes associated with them. For example, most patients dislike not being able to remove their braces to eat and brush their teeth. The INVISALIGN system moves teeth much more slowly than braces, and is limited in its scope and potential. The ESSIX device requires more training by the orthodontist, and is even more limited in its potential applications.

It is therefore an object of the invention to provide a removable orthodontic appliance system which overcomes the drawbacks of the prior art, embodied in a form which is versatilely adapted to individual patient needs, and which is easy to remove and replace by the patient, when desired.

BRIEF SUMMARY OF THE INVENTION

Broadly stated, the concept behind the device according to the invention is the creation of a type of "removable braces," in which the brackets or other wire holder such as tubes and the wires as well are delivering the forces to the teeth without having to be glued or otherwise semi-permanently fixed to the teeth. Instead of being cemented to the teeth, the for example brackets and wires are attached to a clear aligner. The clear aligner is then sectioned along each individual tooth to create discrete plastic sleeves, each which fits over a respective tooth. The brackets are subsequently attached to the wire, making one continuous, interconnected appliance. In order to retain the plastic sleeve on a corresponding one of the teeth, a clip (for example comprised of metal or other suitable material) is glued for example to the backside of each tooth, not visible from the front. The clip allows the clear plastic sleeve to adhere firmly to the tooth by engagement thereof with the lingual surface-mounted clip. There is retention secure enough to maintain the plastic sleeve on the tooth, thereby delivering the forces from the braces to the teeth, but not too much force that the patient is unable to remove the appliance with his/her fingers.

The invention will find utility in treating and correcting mild to moderate malocclusions of both the maxilla and mandible, addressing the needs of retreating patients who have previously received orthodontic treatment and have experienced relapse and/or can be used as a retainer to stabilize the teeth.

Fabrication and installation of the orthodontic appliance in accordance with an embodiment of the invention will be described in detail, with reference to drawings.

DETAILED DESCRIPTION OF THE PREFERRED EMBODIMENTS

Figure 1:
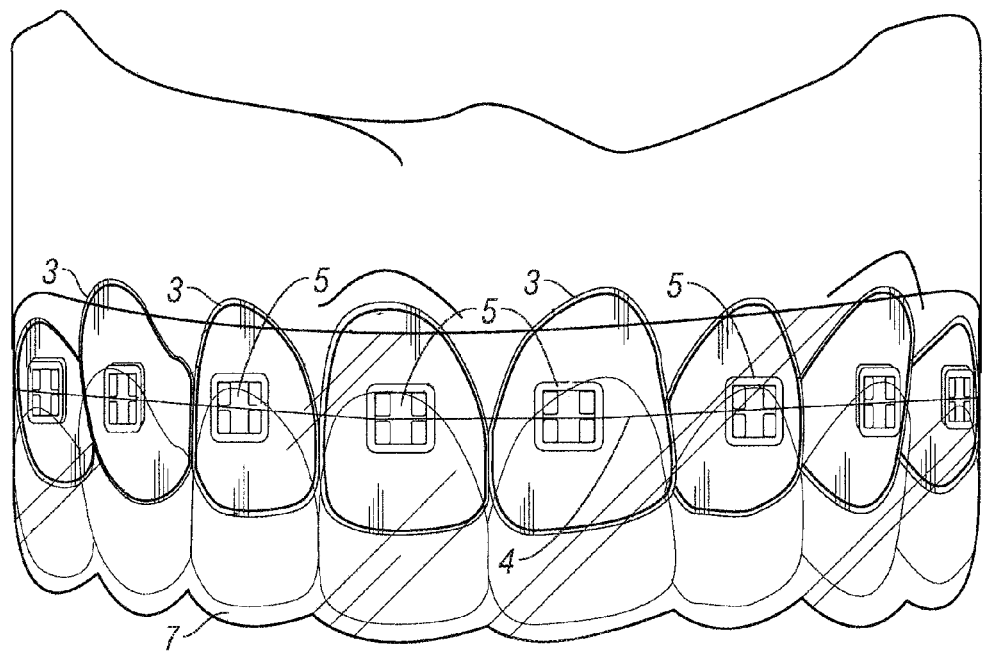
FIG. 1 shows the orthodontic appliance installed on the teeth of a patient and a custom aligner which serves as an insertion and removal tool.

The orthodontic appliance system according to an embodiment of the invention requires initial preparation and fitted installation for each patient on an individual basis. The method of fitting a patient with the system is described in the following.

To begin the process, a polyvinyl siloxane (PVS) impression of the dental arch to be treated is taken. It is also possible to obtain a model of a patient's mouth via an intraoral scanner. The file is then transmitted to a 3D or CAD CAM printer and a replica is created. The impression is subsequently poured in high-strength orthodontic stone, and separated from the impression once the stone is set. The FA point on the buccal surface of the teeth where the ideal bracket location will be is marked on the casting, for example, using a thin pencil to lightly mark surface. Lingual clips can be removably attached to the back (lingual) surfaces of the cast teeth using a temporary adhesive. An example of a suitable adhesive is THERMACURE (Reliance Orthodontics), as is used in the indirect bracketing technique, or any type of temporary adhesive that will keep the lingual clip attached during the plastic thermoforming process, but will allow for the clip to release from the dental cast once embedded in the plastic, as will be described below.

The lingual clips advantageously have a mesh base similar to a conventional bracket, and a square projection that permits the plastic, when heated and pliable, to form over it. Once the plastic has cooled and is firm, the projection acts as a hook that the plastic clips onto, serving as a type of snap-fit engagement. The plastic is rigid, but has some flexibility, which allows the plastic sleeve to deform slightly as the sleeve is pushed in a direction of the gumline, over the lingual clip, and then to snap onto or around the sleeve once it has been completely seated. The inherent rigidity of the plastic then keeps the sleeve tightly adapted to the lingual clip until the patient or doctor grabs the sleeve and lifts it up and over the clip to remove the sleeve.

A sheet of plastic material of suitable thickness is thermoformed over the dental cast with the lingual clips in place. A suitable material is, for example, a 1.0 mm thick C+, A+ or ACE ESSIX plastic sheet. There are also several other different types and brands of plastic available for the dental market. Each plastic was designed and created for a different purpose, and they possess unique properties which may be found particularly useful depending on the individual application. The invention, however, is not contemplated as being limited to these known plastics. As new plastics are developed with improved characteristics, these can be adapted to the inventive orthodontic appliance without departure form the invention.

While the thermoformed plastic is still warm, an instrument is used to tightly adapt and conform the plastic around the lingual clips, ensuring an accurate fit. It is noted that both types of thermoforming machines currently in use, i.e., vacuum or pressure, can be used to fabricate the clear aligner. As with INVISALIGN, digitization and stereolithography can alternatively be optionally be used to fabricate the clear aligner.

Once the plastic has cooled, the gross excess is trimmed away from around the dental cast. Using marks (e.g. pencil) previously placed on the cast, a bracket 5 (see e.g. FIGS. 1 and 2) is attached to each portion of the clear aligner corresponding positionally to each tooth. Advantageously, the base of an orthodontic bracket 5 is heated until it just starts to glow, and it is then pushed into the plastic at the ideal location indicated by the marking viewed through the plastic. As the plastic melts, it flows into the micromesh of the bracket, and mechanically locks the bracket 5 into place by captive engagement. The bracket 5 is now tightly adapted to the buccal surface of the tooth as if it had been bonded to the tooth directly, as with traditional braces. The same process is repeated again for appliances that use wires on both the buccal and lingual sides.

An alternate method to the above, is to bond the brackets to the clear aligner using suitable glue, for example, an epoxy-based adhesive. Using a similar technique as with bonding to real teeth, the bracket is roughened, primed and bonded to the plastic in the ideal location. It is noted, however, that in using this alternative approach, since the bracket is not at least partially embedded in the plastic, the thickness of the plastic causes the bracket to protrude farther forward from the tooth. It is also feasible to create the entire appliance in plastic via the stereolithography technique. The sleeve, retention and "bracket" portion can all be in plastic fabricated as one unit. A small metal insert can then be glued into the plastic "bracket" portion.

Once these procedures are completed, a second piece of plastic is thermoformed over the cast, with the aligners clips and brackets in place (no wire yet being present). This forms a second custom aligner 7, which is advantageously relatively thick but flexible, and which will serve as an insertion and removal tool for the patient, as will be explained. The second tray-shaped aligner 7 is then set aside until the appliance is ready to be inserted.

Figure 3:
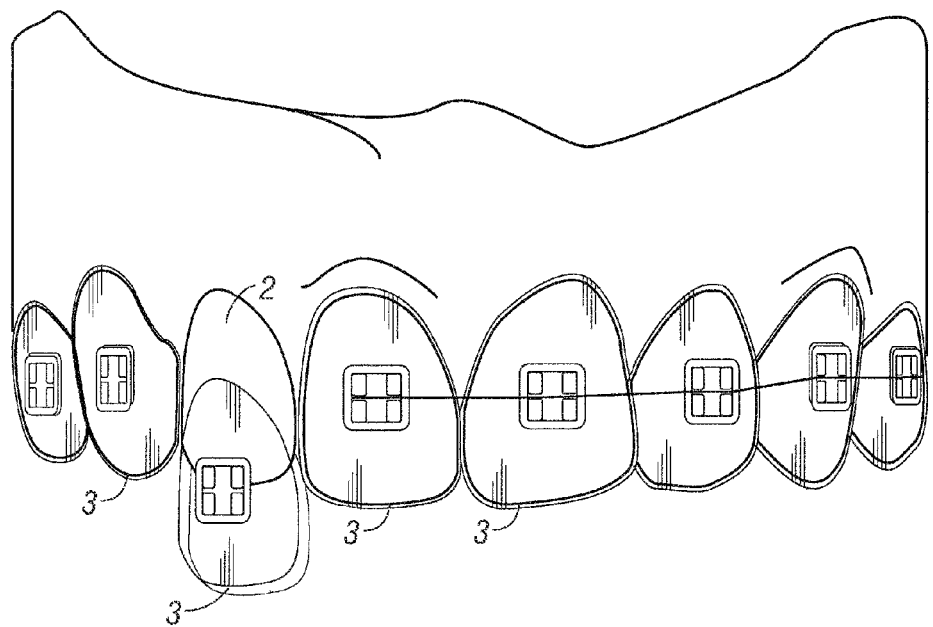
FIG. 3 shows the individual sleeves of the orthodontic appliance according to the invention.
Figure 4:
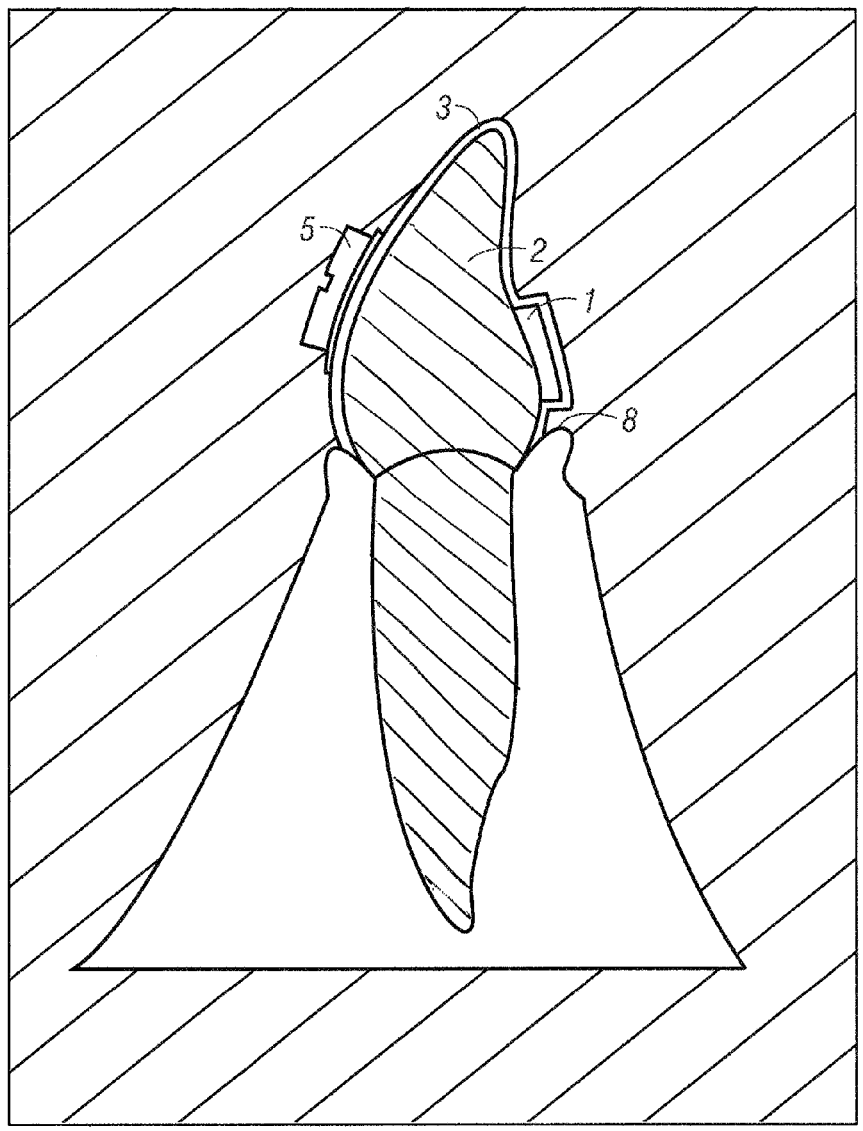
FIG. 4 is a cross-sectional view of a tooth to which a sleeve is installed and held thereto by a lingual clip.
Figure 5:
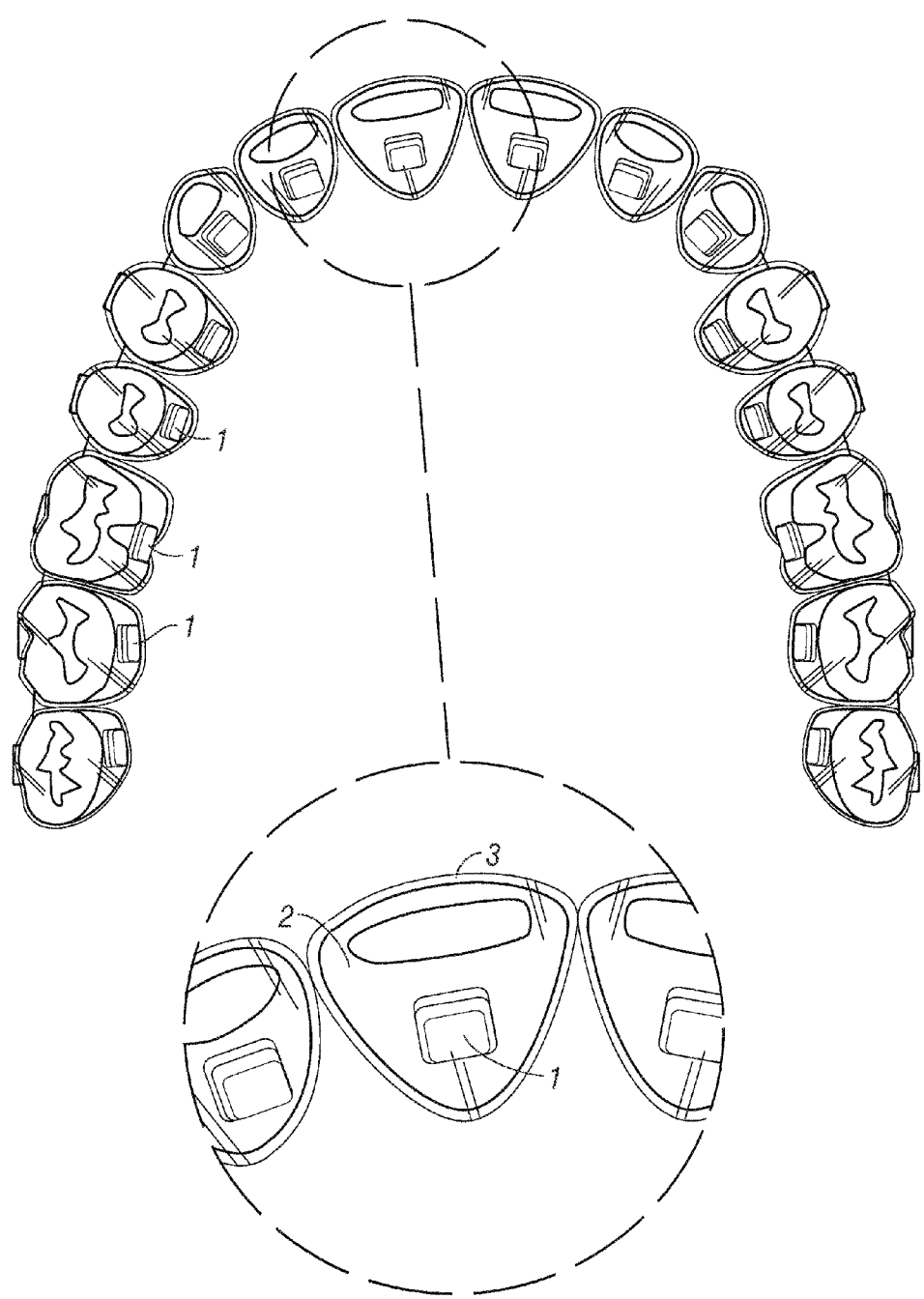
FIG. 5 is a view of the installed orthodontic appliance showing the lingual surfaces of the teeth in detail.

With the brackets attached to the clear aligner, sections of the clear aligner that correspond to the individual teeth are cut out, forming discrete sleeves 3 (see e.g. FIG. 3), each being receivable on a corresponding tooth 2. This can be done, for example, with a dental handpiece, scalpel, scissors or the like. Advantageously, at least about 1-2 mm of excess plastic is maintained beyond the gingival margins (see FIG. 4).

Each sleeve 3 is removed from the cast to ensure that the cuts are sufficient, and that each tooth 2 has its own corresponding individual plastic sleeve 3. The lingual clips (shown attached to the patients teeth in a subsequently described manner in FIG. 4) embedded inside the plastic will likely be detached from the cast during this process. With each plastic sleeve 3 off of the cast, the metal pad of the lingual clip 1 is sandblasted to remove any of the temporary adhesive used during the thermoforming process.

Now, work on the patient can be commenced. The lingual clips 1 are bonded to the lingual surface of the patient's teeth 2. Conveniently, using the same bonding technique as with braces, the tooth surface is etched and primed. Orthodontic bracket cement is applied to the metal pad of the clip 1 positioned inside the plastic sleeve 3 one tooth at a time. The sleeve 3 is placed onto the tooth 2 ensuring that the sleeve 3 is seated completely onto the tooth 2. Using finger pressure, the plastic sleeve 3 is pinched to ensure that the metal pad of the clip 1 is tightly adhered to the lingual surface of the tooth 2. Using a dental curing light, the orthodontic cement is light cured according to the cement manufacturer's recommendations. This process is continued for each sleeve 3 until all of the lingual clips 1 have been bonded to the teeth. The sleeves 3 can then be removed, leaving the lingual clips 1 attached to the teeth 2.

Figure 2:
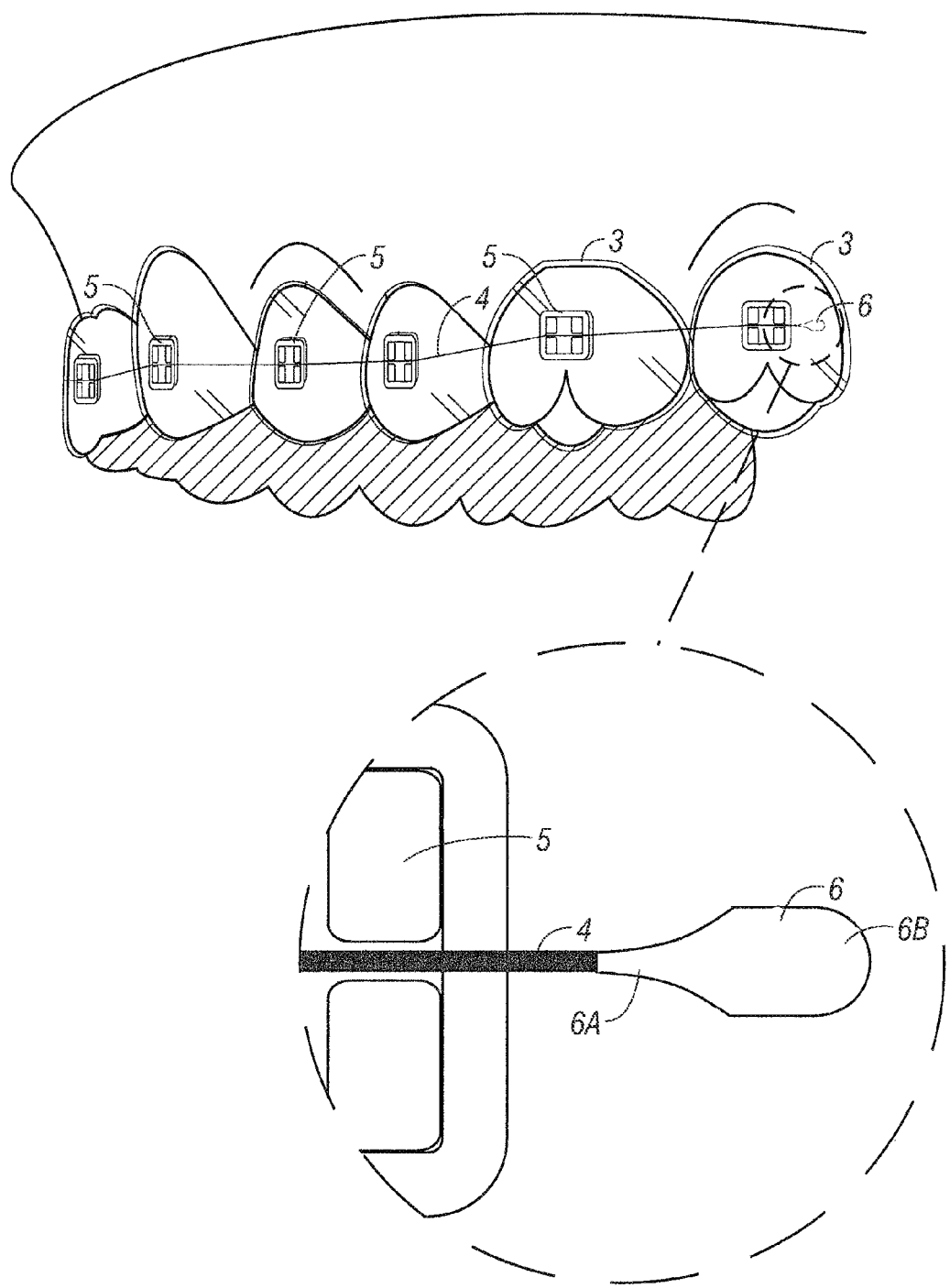
FIG. 2 shows attachment of an arch wire to the buccal brackets of the orthodontic appliance in accordance with the invention.

As depicted in FIG. 2, the sleeves 3 are then reinstalled to the stone impression cast. An orthodontic wire 4 (usually made of nickel-titanium) is sized and cut, and ligated into the brackets 5. An appropriate ball attachment 6 is advantageously attached to the excess wire 4 at the end of the brackets 5 on either side. This ball attachment 6, while not essential to the invention, serves as an advantageous feature of the invention, and which is designed to keep the plastic sleeves 3 from sliding off the ends of the wire 4 when removed from the impression cast or the patent's teeth. This ball attachment 6 acts as a cap to the wire 4, and has one hollow end 6a with a diameter just larger than the corresponding arch wire 4. The other end 6b of the attachment 6 forms a small round ball shape that is smooth and comfortable to the patient. The end of the arch wire 4 is inserted into the hollow end 6a and the narrow portion of the attachment 6 is crimped or pinched around the arch wire 4 to keep it in place.

The second, flexible insertion tray 7 is now placed over the cast and used to pick up the sleeves 3 that are now attached to the wire 4. The plastic sleeves 3 have a tendency to spin around the wire 4 during removal and insertion, and this second plastic tray fits around the sleeves 3 and brackets 5 affording more efficient insertion and removal of the new appliance, by retaining general alignment of the discrete sleeves 3. The insertion tray 7 is then fitted over the teeth 2 inside the patient's mouth, using firm pressure to seat the plastic sleeves 3 onto the teeth. Once at least partially seated, the outer insertion tray 7 is peeled off of the plastic sleeves 3, and using fingers, the sleeves 3 are pushed completely onto each tooth 2 until a click is felt or heard, indicating snap fit engagement of each sleeve 3 to a corresponding one of the lingual clips 1.

The patient wears the appliance as instructed by the orthodontist and uses the outer tray 7 to remove the appliance when eating and brushing. The patient returns for periodic appointments. As the teeth align, the orthodontist advances and progresses the treatment in the same manner as would be done with traditional braces.

Once treatment is completed, the appliance can be worn as a retainer to stabilize treatment as directed by the orthodontist.

It is to be understood that the above disclosure represents one example of the mode by which the invention can be practiced. Other, alternative means for accomplishing the goals disclosed herein can be utilized within the contemplated scope invention, without departure from the spirit of the invention.

For example, the precise nature of the lingual clip 1 need not be limited to that of the above described example. The lingual clip 1 may be evolved into two separate parts; one male and one female. The female attachment would, for example, be bonded to the tooth, to be smaller, and less prominent. It could conceivably house a locking mechanism adapted to receive the male attachment embedded in the plastic sleeve.

In addition to the lingual clip 1, a small mound of dental composite could be added to the facial surface of the teeth below the bracket for added retention.

Additionally, while the invention as disclosed above utilizes stainless steel brackets 5 attached to the plastic sleeves 3, alternatively, clear plastic or ceramic brackets may be utilized for a more esthetic option for the patient.

In accordance with a further alternative example, a lingual bracket may be incorporated into the sleeve on the lingual side of the appliance. A lingual archwire can then be used congruently with the buccal archwire to deliver better forces to the teeth thereby achieving faster treatment times.

It is noted that the appliance according to an embodiment of the invention will be applicable as a long-term retention solution. In such use, the lingual clips will remain on the lower anterior teeth and the appliance will be worn at night. If the patient forgets to wear the appliance or experiences relapse, the wire will deflect slightly to accommodate for the misalignment of the teeth and bring them back into alignment. This is a departure from conventional fixed retainers which have to be remade if the teeth shift. The invention according to this embodiment also serves as an advancement over conventional fixed retainers, insofar as being able to remove the retainer will improve brushing and oral hygiene.

Finally, unlike traditional braces, the orthodontist can remove the appliance during the periodic appointments to change wires and make adjustments. An additional model or cast, with lingual clips, can be fabricated and kept by the orthodontist for the adjustment appointments.

What is claimed is:

1. A method of fitting a patient with a removable orthodontic appliance to move a patient's teeth, comprising:
   taking an impression of a dental arch to be treated;
   pouring the impression to create a dental casting;
   marking a point on a buccal surface of the dental casting indicative of a desired bracket location;
   removably attaching lingual clips to a lingual tooth surface of the dental casting;
   thermoforming a plastic sheet over the dental casting with said lingual clips in place;
   tightly adapting the thermoformed plastic sheet, while still warm, around the lingual clips to form a clear aligner;
   trimming away gross excess plastic of the clear aligner from around the dental casting;
   attaching a bracket to the clear aligner at a position corresponding to said marking;
   cutting sections of the clear aligner that correspond to individual teeth to form discrete sleeves, each of said sleeves being receivable on a corresponding tooth;
   removing each of the sleeves from the dental casting;
   bonding the lingual clips to the lingual surface of the patient's teeth while the sleeve is placed onto the tooth;
   reinstalling the sleeves to the dental casting; and
   ligating an orthodontic wire to each bracket.

* * * * *